(12) United States Patent
Jorczak et al.

(10) Patent No.: US 8,499,761 B2
(45) Date of Patent: *Aug. 6, 2013

(54) REMOTE CONTROL FLUID REGULATION SYSTEM

(75) Inventors: Kevin D. Jorczak, Florence, MA (US); Matthew T. Kling, Uxbridge, MA (US); David S. Green, Boston, MA (US); Leonard Polizzotto, Alexandria, VA (US)

(73) Assignee: Remcore, Inc., Boston, MA (US)

( * ) Notice: Subject to any disclaimer, the term of this patent is extended or adjusted under 35 U.S.C. 154(b) by 264 days.

This patent is subject to a terminal disclaimer.

(21) Appl. No.: 12/795,332

(22) Filed: Jun. 7, 2010

(65) Prior Publication Data

US 2010/0237265 A1 Sep. 23, 2010

Related U.S. Application Data

(63) Continuation of application No. 10/988,217, filed on Nov. 12, 2004, now Pat. No. 7,753,049, which is a continuation-in-part of application No. 10/714,467, filed on Nov. 14, 2003, now Pat. No. 7,552,731.

(51) Int. Cl.
*A61M 11/00* (2006.01)

(52) U.S. Cl.
USPC .............................. 128/205.24; 128/204.21

(58) Field of Classification Search
USPC .............. 128/204.18, 204.21–204.24, 205.24
See application file for complete search history.

(56) References Cited

U.S. PATENT DOCUMENTS

| | | | |
|---|---|---|---|
| 4,834,137 A | 5/1989 | Kawaguchi et al. | |
| 5,103,814 A | 4/1992 | Maher | |
| 5,137,046 A | 8/1992 | Sollman et al. | |
| 5,603,315 A | 2/1997 | Sasso, Jr. | |
| 5,755,224 A | 5/1998 | Good et al. | |
| 5,813,655 A | 9/1998 | Pinchott et al. | |
| 5,839,434 A | 11/1998 | Enterline | |
| 5,865,174 A | 2/1999 | Kloeppel | |
| 5,873,359 A | 2/1999 | Zapol et al. | |
| 5,890,490 A | 4/1999 | Aylsworth et al. | |
| 5,928,189 A | 7/1999 | Phillips et al. | |
| 6,142,149 A * | 11/2000 | Steen ........................ | 128/204.23 |
| 6,192,883 B1 | 2/2001 | Miller, Jr. | |

(Continued)

FOREIGN PATENT DOCUMENTS

WO WO 2005/048906 6/2005

OTHER PUBLICATIONS

PCT/US2004/037700 International Preliminary Report on Patentability dated Oct. 25, 2007, pp. 1-5.

(Continued)

*Primary Examiner* — Steven Douglas
(74) *Attorney, Agent, or Firm* — Holland & Knight LLP; Brian J. Colandreo, Esq.; Michael T. Abramson, Esq.

(57) ABSTRACT

A fluid regulation system comprising a fluid source and a tube operatively connected to the source configured to deliver the fluid from the source to a site. A valve is configured to control a rate of fluid delivered from the source to the site via the tube, and a remote control unit is configured to enable a user to control the valve to adjust the rate of fluid delivered from the source to the site.

77 Claims, 5 Drawing Sheets

U.S. PATENT DOCUMENTS

| | | |
|---|---|---|
| 6,371,114 B1 | 4/2002 | Schmidt et al. |
| 6,427,967 B1 | 8/2002 | Evans |
| 6,467,505 B1 | 10/2002 | Thordarson et al. |
| 6,470,885 B1 | 10/2002 | Blue et al. |
| 6,616,606 B1 | 9/2003 | Petersen et al. |
| 6,763,832 B1 | 7/2004 | Kirsch et al. |
| 7,225,809 B1 | 6/2007 | Bowen et al. |
| 7,552,731 B2 | 6/2009 | Jorczak et al. |
| 7,720,362 B2 | 5/2010 | Arnold et al. |
| 7,727,156 B2 | 6/2010 | Angelsen et al. |
| 7,753,049 B2 | 7/2010 | Jorczak et al. |
| 2005/0126571 A1 | 6/2005 | Jorczak et al. |
| 2010/0074776 A1 | 3/2010 | Ludlow et al. |

OTHER PUBLICATIONS

PCT/US2004/037700 Corrected International Search Report and The Written Opinion dated Nov. 29, 2007, pp. 1-6.

* cited by examiner

REMOTE CONTROL FLUID REGULATION SYSTEM

CROSS-REFERENCE TO RELATED APPLICATIONS

The present application is a continuation of U.S. patent application Ser. No. 10/988,217, entitled REMOTE CONTROL FLUID REGULATION SYSTEM, filed on Nov. 12, 2004, now issued as U.S. Pat. No. 7,753,049 on Jul. 13, 2010, which is a continuation-in-part of U.S. patent application Ser. No. 10/714,467, entitled REMOTE CONTROL GAS REGULATION SYSTEM, filed Nov. 14, 2003, now issued as U.S. Pat. No. 7,552,731 on Jun. 30, 2009. Both are hereby incorporated by reference.

TECHNICAL FIELD

The invention relates generally to a fluid regulation system for regulating and delivering fluids from a source via a valve to a site. In particular, the invention relates to such a system for delivering a fluid to a remote site by means of a remote control unit. There may be a need to regulate levels of such fluids as inert gases, e.g., nitrogen, argon, in a clean room, or to regulate oxygen flow into an oxygen-rich environment. There may also be a need to control the level of toxic fluids, e.g., chlorine, bromine in a tent or other enclosure requiring a germ-free or insect-free environment or to maintain an oxygen-free environment in a room containing combustible materials. It may be also be necessary to deliver fluids into potentially hazardous environments. In the proposed system, a remote control unit controls a valve regulating the flow of fluid. The remote control unit allows the individual to adjust the rate of fluid flow.

BACKGROUND

There are many instances where it would be desirable for delivering a fluid to a remote site by means of a remote control unit. There may be a need to regulate levels of inert gases, e.g., nitrogen, argon, in a clean room, or to regulate oxygen flow into an oxygen-rich environment. There may be a need to control the level of toxic fluids, e.g., chlorine, bromine in a tent or other enclosure requiring a germ-free or insect-free environment or to maintain an oxygen-free environment in a room containing combustible materials. One instance of particular note is the delivery of supplemental oxygen to a patient experiencing chronic difficulties in breathing. In some instances, such individuals may suffer from diminished oxygen uptake into the body. For example, the lungs of such individuals are not able to transfer oxygen into the blood stream sufficiently and are aided in doing so by increasing the partial pressure of oxygen in the alveoli. Regardless of the cause of the pulmonary ailments, even a partial disability of the pulmonary system may require enrichment or supplementation of oxygen. In extreme instances, a severely compromised respiratory system may be incapable of supplying the necessary oxygen level for an individual. As a result, supplemental oxygen must be delivered to such an individual to maintain the amount of oxygen at an acceptable level. The supplemental amount needed will vary depending upon the activity level of the patient.

Other examples where it would be useful to provide a controlled delivery of a fluid from a remote site with a remote control device include an instrument driven clean room. When robotics replace the human element in a clean room, it may also allow the replacement of a breathable atmosphere with an atmosphere comprising mostly of inert gases to avoid oxidation of elements sensitive even to atmospheric levels of oxygen, such as semiconductors.

Another example of the need to regulate fluid level or concentration from a remote site is the "tenting" of habitable structures to rid them of germs, insects, vermin or other undesirable elements. To be able to control the level of fluids maintained in a tented environment sufficient to perform the task required without endangering the atmosphere outside the tent is a desirable feature of remote control of fluid inputs.

The industrial applications for the remote control of fluid delivery are seemingly endless. In almost any situation where there is a need to deliver fluid into a room or other controlled area where the health and/or safety of an individual would be compromised by entry into the controlled area, fluid delivery controlled from a remote location is a desirable and preferred alternative. Another example that comes to mind is the delivery of oxygen rich fluids into an area of combustible materials. Another example is the remote delivery of chemicals to treat sewage.

As a result, devices and systems for regulating the remote delivery of fluids are known in the art. For example, in the delivery of supplemental oxygen, a stationary source of oxygen is provided having a tube attached thereto for supplying oxygen to the individual. The source may be a tank reservoir containing pressurized medical quality oxygen. A flow regulator comprising one or more adjustable valves may be provided at the source to control the rate of oxygen flow from the tank through the tube to deliver oxygen to the patient by way of a nasal cannula, breathing mask, or transtracheal oxygen delivery system.

In general, there are two categories of fluid regulation systems, continuous flow and condition-responsive flow. As alluded to above, continuous flow devices and systems are generally set at a flow rate that provides continuous fluid flow to the site, regardless of the immediate need for fluid input. A continuous flow device and system for supplemental oxygen is generally described in U.S. Pat. No. 6,467,505 to Thordarson et al. A drawback associated with a system such as described in the above noted patent is that that the user benefits primarily from the supplemental oxygen during times in the respiratory cycle when the patient is inhaling. At other times, the supplemental oxygen released is of minimal benefit. Thus, when a continuous flow system uses fluid holding tanks of finite volume, such a system requires more frequent refilling and/or changing of the tanks.

In the alternative, condition-responsive systems are employed to extend the time that a system may receive fluid by providing fluid to a system only when the system generates a fluid input signal. For example, a pulsed flow device for oxygen input is described, for example, in U.S. Pat. No. 5,839,464 to Enterline. In the system described, a burst of oxygen is delivered into a patient's nasal passages when a patient begins to inhale. A condition-responsive system operates on pre-set conditions designated by the user. Such pre-set conditions do not allow the flexibility needed in a dynamically changing environment. For example, combustible fuels introduced into an oxygen-rich environment may require multiple and dynamically changing conditions to maintain a safe environment.

When a stationary source of fluid is provided, fluid delivery is initiated by setting a flow rate for a delivery device at the source prior to initiating a sequence of fluid delivery. This is inconvenient when the regulator is out of reach. In addition, when the individual is away from the source, changes in the fluid flow rate cannot be effected. Thus, using this type of stationary fluid delivery system often maintains the fluid flow rate at a higher or lower level than necessary, causing insufficient delivery rates at times and excessive delivery rates at other times.

In some instances, known systems and devices automatically adjust the fluid flow rate to a system. A system responsive to dynamic changes in system requirements includes a fluid source, a means for fluid delivery, a fluid destination point and a valve for delivering fluid from the source to the destination point at multiple flow rates. A sensor is provided at the destination point to sense fluid parameters, e.g., volume, temperature flow rates, and to adjust the valve according to the sensed parameter.

One unavoidable drawback of automatically adjustable devices and systems is that they require a sensor for operability. For example, when the sensor is used to monitor the user's respiration, the sensor may be placed in user's nose, elsewhere in the user's respiratory tract, or on the user's face for detecting the flow of oxygen. As another example, when the sensor is used to monitor the user's physical activity, motion sensor detectors often must be placed on or near regions of the user's body engaging in physical activity. As a further example, when the sensor is used to monitor the user's blood oxygen content, invasive techniques for obtaining blood or for positioning the sensor may be required. The sensors generally represent a source of discomfort or irritation for the user.

Another drawback for such devices and systems is that automatic adjustment mechanisms are often imperfect. Often, the response times associated with such mechanisms are inadequate and result in the delayed adjustment of fluid delivery.

Thus, there is a need in the art to overcome the shortcomings associated with known fluid regulation technology by providing a system for delivering a fluid that includes a remote control unit to allow a user to adjust the delivery rate of fluid flow.

The remote controlled system of this invention can be applied to both a demand release valve or a continuous flow valve. With the demand valve, it would be used to tell when to start and stop fluid flow. When used with a continuous flow system, it can be used to regulate the flow rate.

SUMMARY OF THE INVENTION

In a first embodiment, the invention relates to a fluid regulation system comprising a source of a fluid, a tube in communication with the source for delivering the fluid from the source to a site, and a valve for controlling the rate of fluid flow from the source to the site. A remote control unit for controlling the valve is also provided to allow the individual to adjust the rate of fluid flow from the source through the tube to the site. Typically, the system excludes any means for automatically adjusting the rate of fluid flow from the source through the tube to the site. The invention is particularly useful when the valve is out of the user's reach.

In the first embodiment, the invention is used to deliver medical fluid comprising oxygen at a concentration greater than atmospheric oxygen concentration.

In another embodiment, the invention provides a method for delivering a breathable fluid to an individual. In the use of the method, breathable fluid is directed from a source of the breathable fluid through a valve and a tube to an individual for inhalation, wherein the valve is adapted for controlling fluid flow from the source and is not automatically adjusted according to the level of physical activity of the individual. In addition, the individual is allowed to adjust the rate of fluid flow from the source using a remote control unit for controlling the valve independently from any inhalation activity by the individual flow. The method typically involves adjusting the flow rate during various activities to correspond to a flow rate prescribed by a medical professional such as a physician. The prescribed flow rates may be associated with the individual's need for the breathable fluid at rest, with moderate activity, or with strenuous activity.

In a further embodiment, the invention relates to a fluid regulation system for delivering fluid from a source containing a fluid to a site. A valve is provided comprising an inlet adapted to receive fluid from the source; an outlet is adapted to deliver fluid to the site, a means for altering fluid flow from the inlet to the outlet, and a receiver for receiving a signal for controlling the means for altering fluid flow. Also provided is a remote control unit for transmitting the signal for controlling the means for altering fluid flow at a distance from the source of the fluid.

DETAILED DESCRIPTION OF THE INVENTION

Figure 1A:
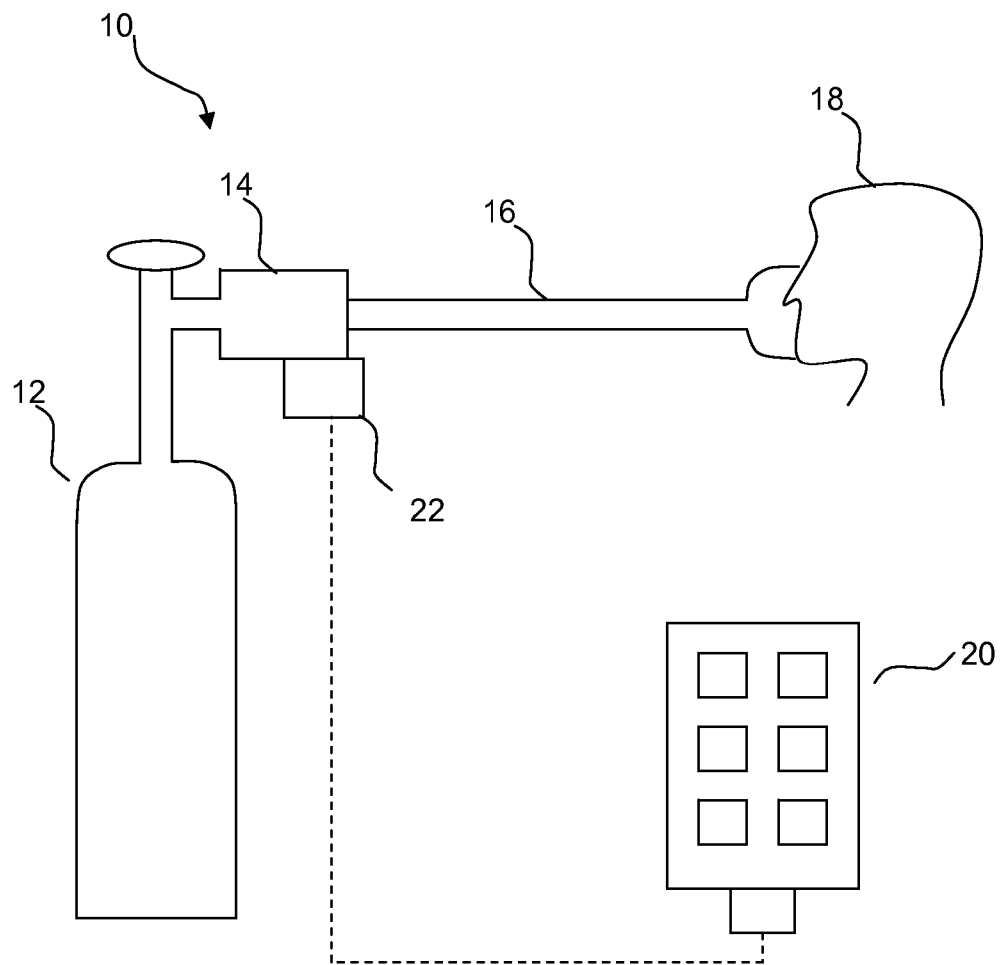
FIG. 1A is a schematic illustration of an exemplary fluid regulation system of the present invention.

Before the invention is described in detail, it is to be understood that, unless otherwise indicated, this invention is not limited to particular materials, components or manufacturing processes, as such may vary. It is also to be understood that the terminology used herein is for purposes of describing particular embodiments only, and is not intended to be limiting.

As used in the specification and the appended claims, the singular forms "a," "an" and "the" include plural referents unless the context clearly dictates otherwise. Thus, for example, reference to "remote control unit" includes a single remote control unit as well as a plurality of remote control units, reference to "an inlet" includes a single inlet as well as multiple inlets, and reference to "a valve" includes a single valve as well as an assembly of valves, and the like.

In this specification and in the claims that follow, reference will be made to a number of terms that shall be defined to have the following meanings, unless the context in which they are employed clearly indicates otherwise:

The term "activity" is used herein in its ordinary sense to refer to the state or energy associated with an individual's body movement. Thus, for example, the term "physical activity" typically refers to the state or energy associated with the movement of an individual's body, resting, walking, lifting, climbing, etc. as distinguished from activity of the mind. Similarly, the term "inhalation activity" refers to the state or energy associated with an individual's drawing in of a breathable fluid through the act of respiration.

The terms "automatic" or "automatically" are used in their ordinary sense to refer to actions or operations that take place independently from an individual's control. For example, "automatic" adjustment the flow rate of fluid to an individual according to the level of the physical activity of the individual occurs independently from conscious input by the individual.

The term "fluid" defines a liquid or a gas as well as an admixture of both. For example, an inert gas such as argon or nitrogen is referred to herein as a fluid. Oxygen may be referred to herein as either a fluid or a gas.

The term "frequency hopping" is used herein to describe a technique typically associated with wireless signal transmission methods, wherein a signal is initially transmitted at a first frequency and later transmitted at a different frequency to provide a mechanism for low probability of intercept and resistance to jamming.

"Optional" or "optionally" as used herein means that the subsequently described feature or structure mayor may not be present—or that the subsequently described event or circumstance mayor may not occur. The description includes instances where a particular feature or structure is present and instances where the feature or structure is absent, or instances where the event or circumstance occurs and instances where it does not. Mere reference to a feature, structure, event or circumstance as "optional," does not imply in any way whether the feature, structure, event or circumstance is be preferred.

The term "remote control unit" in its ordinary sense refers to a unit capable of controlling a machine or apparatus from a distance. As used herein, the term typically refers to a unit for controlling a valve that controls flow of fluid flow from a source to a site. In one preferred embodiment of the present invention, the term refers to a unit for controlling a valve that controls flow of breathable gas from a source to an individual.

The term "substantially" as in "substantially constant flow rate" is used herein to refer to a flow rate that does not differ by more than approximately 15%. Preferably, the flow rates do not differ by more than 5% and optimally by not more than approximately 1%. Other uses of the term "substantially" have an analogous meaning.

In general, the invention fulfills the need for a fluid regulation system that allows an individual to control, remotely or otherwise, the delivery of fluid, to a site on an as-needed and/or desired flow rate. In certain embodiments, a source of a breathable fluid has a tube in communication therewith for delivering the breathable fluid from the source to an individual. A valve controls the rate of fluid flow from the source to the individual, and a remote control unit controlling the valve to allow the individual to adjust the rate of fluid flow from the source at a distance from the individual through the tube to the individual independently from any inhalation activity by the individual. The system provided overcomes the drawback associated with known devices by excluding any means for automatically adjusting the rate of fluid flow from the source through the tube to the individual according to the level of physical activity of the individual. In certain embodiments suited for industrial applications, a source of fluid has a tube in communication therewith for delivering the fluid from the source to an industrial site, such as a clean room or a hazardous substance site. A valve controls the rate of fluid flow from the source to the site, and a remote control unit controls the valve to allow the unit operator to adjust the rate of fluid flow from the source through the tube to the site.

Systems for delivery of fluids such as breathable gases are well suited for use in conjunction with "ramp-down" and "fail-safe" operation by individuals having a compromised respiratory system, particular during changes in activity level. For example, patients who suffer from COPD need externally delivered oxygen therapy at an appropriate rate in order to breathe correctly, both at home and in hospitals. For these patients, physicians often prescribe different oxygen flows for different activities, e.g., 2 liters per minute for a patient at rest and 5 liters per minute for a patient engaged in a more vigorous physical activity.

In order to provide such patients control over the rate of oxygen flow according to their activity level, the invention also provides a method for delivering of a breathable fluid to an individual. The method involves remotely directing breathable fluid from a distant source of the breathable fluid through a valve and a tube to an individual for inhalation. The valve is adapted for controlling fluid flow from the source and allowing the individual to adjust the rate of fluid flow from the source using a remote control unit for controlling the valve independently from any inhalation activity by the individual.

To avoid the disadvantages associated with known devices, the rate of fluid flow is not automatically adjusted by the system according to the level of physical activity of the individual. Instead, the invention allows the individual to adjust the flow rate to a prescribed or desired flow rate, e.g., associated with the individual's need for the breathable fluid at rest, with moderate activity, or with strenuous activity.

In an industrial setting, the invention provides a method for delivering of a fluid to a site. The method involves directing from a source of the fluid through a valve and a tube to a site. The valve is adapted for controlling fluid flow from the source and allowing the user to adjust the rate of fluid flow from the source using a remote control unit for controlling the valve.

Figure 1B:
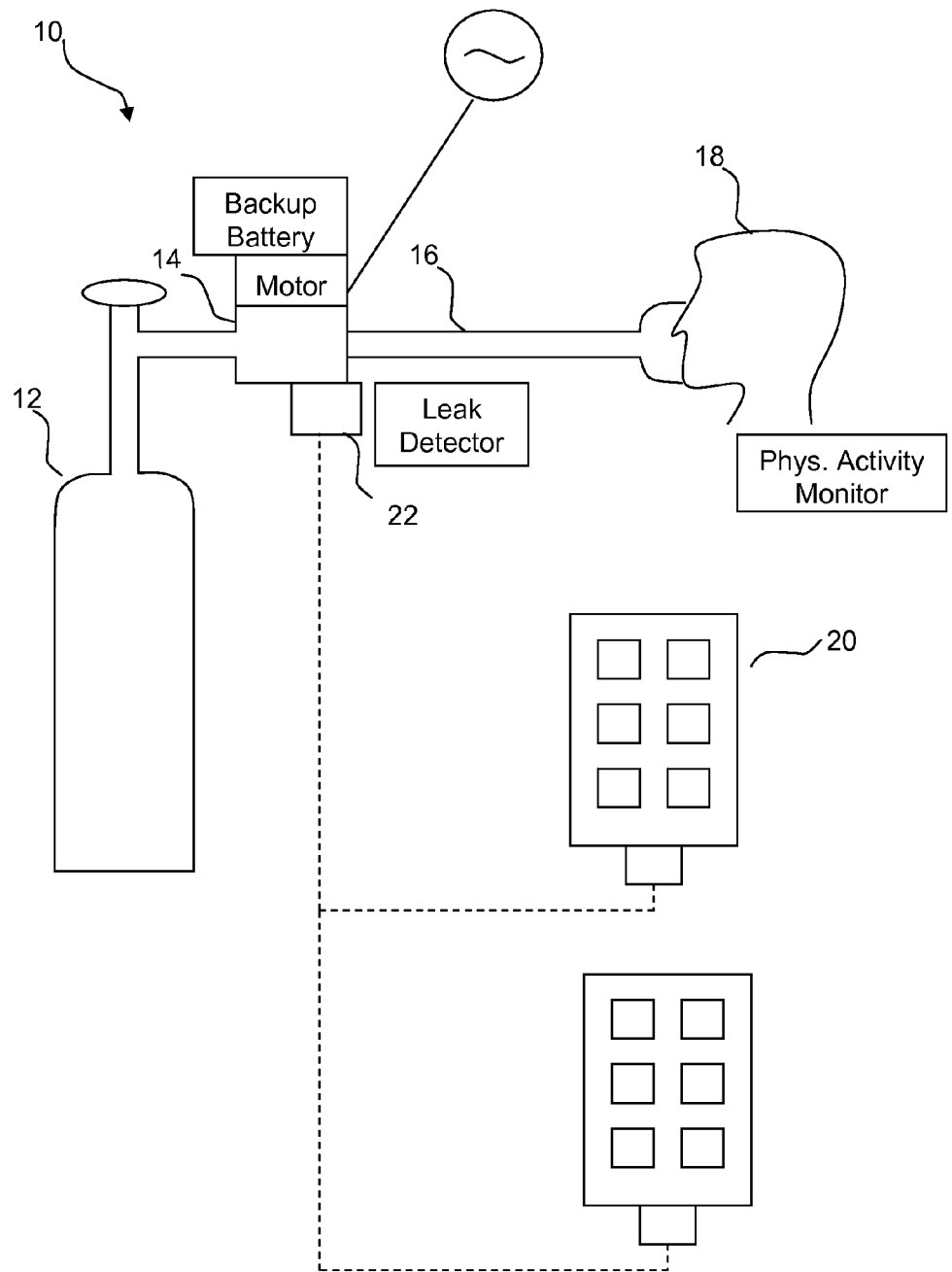
FIGS. 1B and 1C are schematic illustrations of exemplary fluid regulation systems of the present invention showing additional features beyond those depicted in FIG. 1A.
Figure 1C:
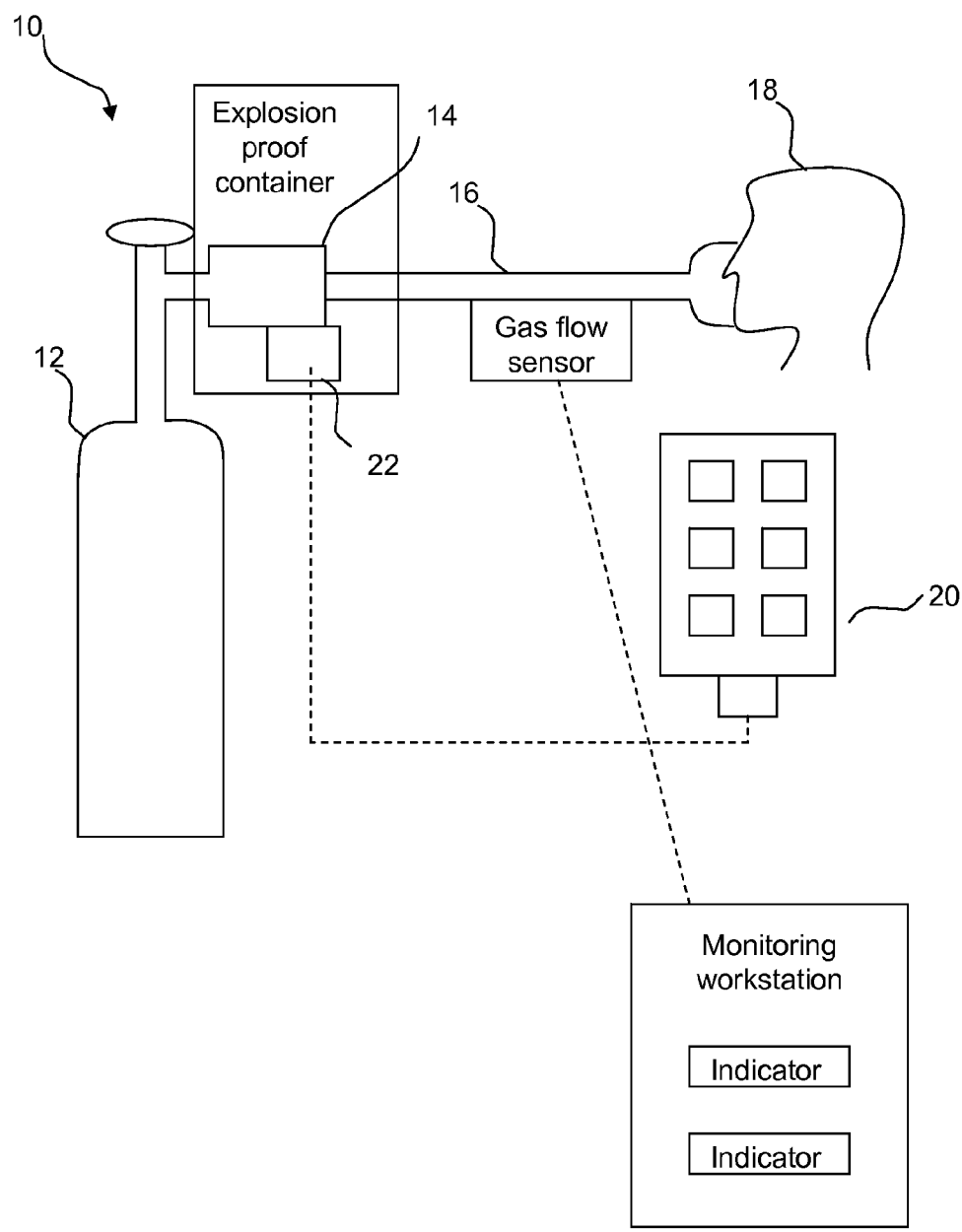

The inventive system contains components typically included in an ordinary oxygen regulation system but also includes a number of modifications. FIGS. 1A-1C depict exemplary embodiments of the inventive system for medical applications. As with all figures referenced herein, like parts are referenced by like numerals, FIGS. 1A-1C are not necessarily to scale, and certain dimensions may be exaggerated for clarity of presentation. As depicted, the system 10 includes a source of oxygen in the form of an oxygen tank 12. An oxygen regulator comprising a solenoid valve 14 is operatively connected and located downstream from the tank 12. A tube 16 is also attached the valve 14 to transport to oxygen to a patient 18. The valve 14 is adapted to control the oxygen flow-rate based on a control signal received thereby.

Also provided is a remote control unit 20 for controlling the valve. Typically constructed as a hand held unit, the control unit 20 is adapted to generate a control signal to allow the patient to select an appropriate oxygen flow rate from the oxygen tank 12. As depicted, the signal is transmitted through a wireless link to a receiver 22 for receiving the control signal. The receiver 22 is depicted in operative communication with the solenoid valve 14. Optionally, a translator is provided to translate the control signal to maintain or alter the flow of oxygen that is delivered through the valve 14 to the patient 18.

The invention is particularly suited for use with a medical fluid such as oxygen, nitrous oxide, medical air, nitrogen, etc. For oxygen therapy, oxygen is generally provided at a concentration greater than atmospheric oxygen concentration. Thus, for example, the source may include a tank containing medical fluid comprised of oxygen. Typically, such tanks are contaminant-free and capable of containing pressured and/or liquefied fluid. Often such tanks are made from steel or aluminum. Steel tanks are typically tested every 10 years for structural damage, whereas aluminum tanks are tested every 5 years for cracks, dents, burns, dings, oil, grease, corrosion, and other type of damage.

Typically, oxygen cylinders provide about 2 L/min to 15 L/min of oxygen. While more expensive, the liquid oxygen tanks can deliver oxygen for four times longer than the normal tanks. In addition or in the alternative, the source may comprise an oxygen concentrator. Concentrators extract oxygen from air for delivery in a concentrated form.

Oxygen regulators may be used to control and reduce the pressure of the oxygen from a tank containing compressed or liquid oxygen for safe and steady fluid delivery to a patient. The regulator typically contains or is used in conjunction with a valve. Such a valves are typically comprised an inlet adapted to receive fluid from the source, an outlet adapted to deliver fluid to the individual, and a means for altering fluid flow from the inlet to the outlet. Although fluid flow through the valve may be altered, the valve is typically constructed so that it is capable of providing a substantially constant flow rate of the fluid flow to the individual.

Any number of known means for altering fluid flow may be employed. Exemplary means for altering fluid flow include, but are not limited to, linearly or rotationally actuated switching mechanisms such as those associated with gate and ball valves, respectively. Typically, the valve is electrically powered and/or actuated. Thus, for example, the valve may be provided comprising a motor in electrical connection with a source of alternating electrical current. In addition or in the alternative, a direct current backup battery may be provided for powering the valve. Additional or alternative means such as hydraulic may be used to power and/or actuate the switching mechanism as well. Regardless of the means employed to power and/or actuate the switching mechanism, it is preferred that the valve be manually operative when the power source is inoperative. For example, in case of an AC power failure, the system should have a battery backup power source, which would allow the system to run for a short period of time while the user switches the electronic system to be bypassed, so that the manual controlled fluid regulator can be used.

As alluded to above, solenoid valves are particularly useful in the invention. Such valves typically employ a coil and a core that slides along under the influence of the magnetic field generated because of electrical current passed through the coil. The core serves as plunger to open or close a valve. Simple solenoid valves provide no control over the degree to which the valve is open or closed. Proportional solenoid valves, on the other hand, uses a variable input voltage and/or current to control the degree to which the valve is open or closed. The applied voltage and/or current are generally proportional to the amount of flow that the valve will provide. Proportional solenoid valves can provide precise regulation of flow, can typically operate anywhere from 0 to about 500 pounds per square inch, are very small and compact, and can operate under fairly rugged conditions.

In general, any remote control unit may be used that is suitable for controlling the valve to allow the individual to adjust the rate of fluid flow from the source through the tube to the individual independently from any inhalation activity by the individual. In some instances, the remote control unit may be attached to the valve, e.g., via a hardwired connection. Alternatively, the remote control unit may be detached from the valve, e.g., wireless. Typically, though, a receiver is provided for receiving a signal from the remote control unit for controlling the valve or for controlling the means for altering fluid flow. Preferably, the signal is electromagnetic in nature, and may include waves of radio frequency, microwave, infrared, and/or visible signal. The signal may be digital or analog. In any case, the system may be equipped for operation using a plurality of control signal frequencies, optionally with frequency hopping capability.

For example, the remote control system may employ a microprocessor-based design to implement a radio frequency (RF) communication set up to provide a wireless data transfer. Along with the remote control, an electro-mechanical element, e.g., a solenoid valve, serves to regulate the flow from the oxygen tank. RF systems can be implemented by using only a small number of electronic devices. These devices may include an antenna, a transmitter module and a receiver module, which are responsible for transmitting a signal. Optionally, the transmitter module modulates and/or amplifies the signal before transmission and the receiver module down-converts and/or demodulates the transmitted signal. Those of ordinary skill in the art will recognize that the selection of an appropriate microprocessor depends on the capabilities of its central processing unit, memory, timer(s), port(s), software and other components. Printed circuit board technology may be employed with the microprocessor-based design described above. In some instances, the remote control system may be adapted to interface with a computer.

To provide an indication of fluid flow rate, the system may further include a fluid flow sensor positioned to detect and/or monitor the rate of fluid flow to a site or to an individual. When such a sensor is employed, an indicator for indicating the rate of fluid flow detected and/or monitored by the fluid flow sensor is typically provided as well. Typically, the remote control unit houses such an indicator. In addition or in the alternative, one or more indicators may be located in a monitoring station, e.g., a nurses' station, as discussed below. In any case, the invention generally allows users to adjust their oxygen flow rates from zero to about 15 liters per minute.

Figure 2:
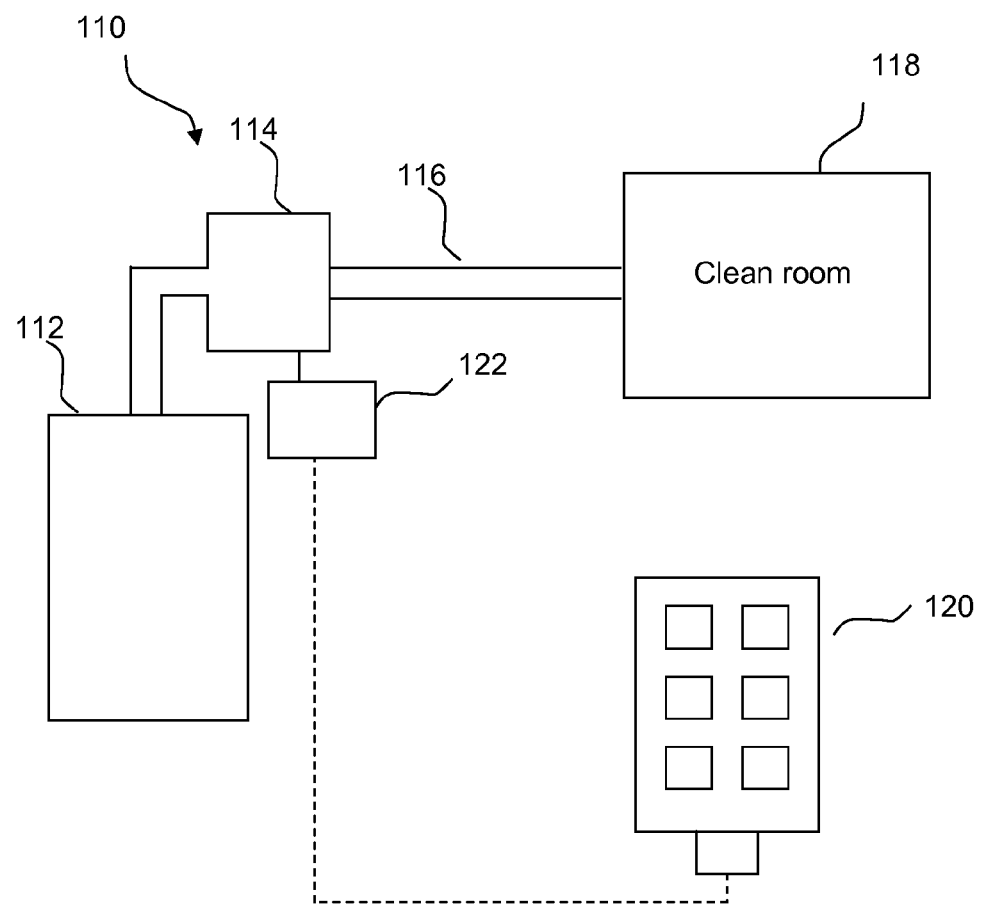
FIG. 2 is a schematic illustration of an exemplary fluid regulation system of the present invention for use in an industrial application, e.g., the delivery of fluids by remote control to a clean room.

FIG. 2 depicts an exemplary embodiment of the inventive system for industrial applications. As depicted, the system 110 includes a source of fluid in the form of a tank 112 containing an inert gas, e.g., argon. A regulator comprising a solenoid valve 114 is operatively connected and located downstream from the tank 112. A tube 116 is also attached the valve 114 to transport to oxygen to a clean room 118 used to manufacture semiconductors for example. The valve 114 is adapted to control the fluid flow-rate based on a control signal received thereby.

Also provided is a remote control unit 120 for controlling the valve. Typically constructed as a hand held unit, the control unit 120 is adapted to generate a control signal to allow the user to select an appropriate fluid flow rate from the tank 112. As depicted, the signal is transmitted through a wireless link to a receiver 122 for receiving the control signal. The receiver 122 is depicted in operative communication with the solenoid valve 114. Optionally, a translator is provided to translate the control signal to maintain or alter the flow of fluid that is delivered through the valve 14 to the clean room 118.

The invention is particularly suited for use with a fluid, e.g., an inert gas such as argon or nitrogen, which enables the user to avoid an atmosphere corrosive to sensitive semiconductor elements. The embodiment of FIG. 2 could also be used to control the level of toxic fluids, e.g., chlorine, bromine in a tent or other enclosure requiring a germ-free or insect-free environment or to maintain an oxygen-free environment in a room containing combustible materials. The system of FIG. 2 also provides the ability to deliver fluids into potentially hazardous environments. The remote control unit of the proposed system controls a valve regulating the flow of fluid. The remote control unit allows the individual to adjust the rate of fluid flow. Other applications of the embodiment of FIG. 2 include the delivery of materials to isolation rooms in which radioactive materials are used.

The industrial applications for the remote control of fluid delivery as set forth in the embodiment of FIG. 2 are seemingly endless. In almost any situation where there is a need to deliver fluid into a room or other controlled area where the health and/or safety of an individual would be compromised by entry into the controlled area, fluid delivery controlled from a remote location is a desirable and preferred alternative. Another example that comes to mind is the delivery of oxygen rich fluids into an area of combustible materials. Another example is the remote delivery of chemicals to treat sewage. There are also instances in the food industry where is it desirable to provide a clean or sterile environment and minimize human contact with foodstuffs. In such instances, a mechanism for remote control delivery of materials would be desirable.

For gases provided at a concentration greater than atmospheric concentration, the source may include a tank containing the inert gas. Typically, such tanks are contaminant-free and capable of containing pressured and/or liquefied fluid. Often such tanks are made from steel or aluminum. Steel tanks are typically tested every 10 years for structural damage, whereas aluminum tanks are tested every 5 years for cracks, dents, bums, dings, oil, grease, corrosion, and other type of damage.

Fluid regulators may be used to control and reduce the pressure of the gas from a tank containing compressed or liquid gas for safe and steady fluid delivery to a clean room. The regulator typically contains a valve or is used in conjunction with a valve. Such a valve is typically comprised of an inlet adapted to receive fluid from the source, an outlet adapted to deliver fluid to the site, and a means for altering fluid flow from the inlet to the outlet. Although fluid flow through the valve may be altered, the valve is typically constructed so that it is capable of providing a substantially constant flow rate of the fluid flow to the site.

Any number of known means for altering fluid flow may be employed. Exemplary means for altering fluid flow include, but are not limited to, linearly or rotationally actuated switching mechanisms such as those associated with gate and ball valves, respectively. Typically, the valve is electrically powered and/or actuated. Thus, for example, the valve may be provided comprising a motor in electrical connection with a source of alternating electrical current. In addition or in the alternative, a direct current backup battery may be provided for powering the valve. Additional or alternative means such as hydraulics may be used to power and/or actuate the switching mechanism as well. Regardless of the means employed to power and/or actuate the switching mechanism, it is preferred that the valve be manually operative when the power source is inoperative. For example, in case of an AC power failure, the system should have a battery backup power source, which would allow the system to run for a short period of time while the user switches the electronic system to be bypassed, so that the manual controlled regulator can be used.

As alluded to above, solenoid valves are particularly useful in the invention. Such a valve typically employs a coil and a core that slides along under the influence of a magnetic field generated because of electrical current passed through the coil. The core serves as plunger to open or close a valve. Simple solenoid valves provide no control over the degree to which the valve is open or closed. Proportional solenoid valves, on the other hand, use a variable input voltage and/or current to control the degree to which the valve is open or closed. The applied voltage and/or current are generally proportional to the amount of flow that the valve will provide. Proportional solenoid valves can provide precise regulation of flow, can typically operate anywhere from 0 to about 500 pounds per square inch, are very small and compact, and can operate under fairly rugged conditions.

In general, any remote control unit may be used that is suitable for controlling the valve to allow the user to adjust the rate of fluid flow from the source through the tube to the site.

In some instances, the remote control unit may be attached to the valve, e.g., via a hardwired connection. Alternatively, the remote control unit may be detached from the valve, i.e., a wireless connection. Typically, though, a receiver is provided for receiving a signal from the remote control unit for controlling the valve or for controlling the means for altering fluid flow. Preferably, the signal is electromagnetic in nature, and may include waves of radio frequency, microwave, infrared, and/or visible signal. The signal may be digital or analog. In any case, the system may be equipped for operation using a plurality of control signal frequencies, optionally with frequency hopping capability.

For example, the remote control system may employ a microprocessor-based design to implement a radio frequency (RF) communication set up to provide a wireless data transfer. Along with the remote control, an electro-mechanical element, e.g., a solenoid valve, serves to regulate the flow from the fluid tank, RF systems can be implemented by using only a small number of electronic devices. These devices may include an antenna, a transmitter module and a receiver module, which are responsible for transmitting a signal. Optionally, the transmitter module modulates and/or amplifies the signal before transmission and the receiver module down-converts and/or demodulates the transmitted signal. Those of ordinary skill in the art will recognize that the selection of an appropriate microprocessor depends on the capabilities of its central processing unit, memory, timer(s), port(s), software and other components. Printed circuit board technology may be employed with the microprocessor-based design described above. In some instances, the remote control system may be adapted to interface with a computer.

To provide an indication of fluid flow rate, the system may further include a fluid flow sensor positioned to detect and/or monitor the rate of fluid flow to the site. When such a sensor is employed, an indicator for indicating the rate of fluid flow detected and/or monitored by the fluid flow sensor is typically provided as well. Typically, the remote control unit houses such an indicator. In addition or in the alternative, one or more indicators may be located in a monitoring station. In any case, the invention generally allows users to adjust fluid flow rates incrementally.

Figure 3:
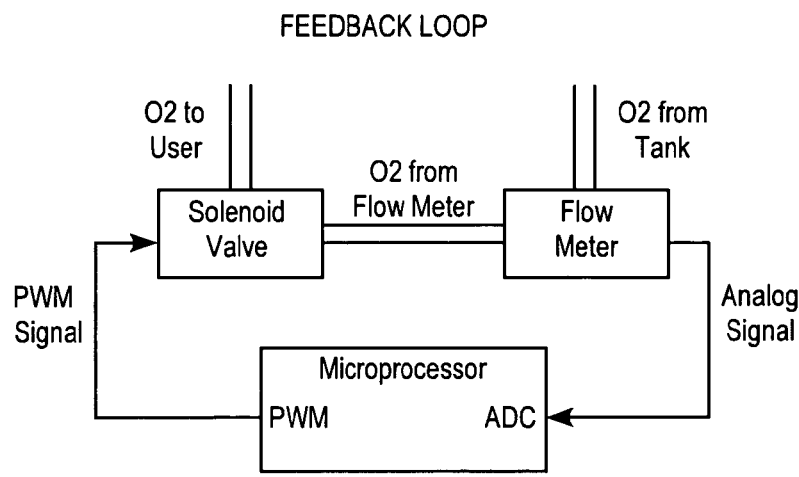
FIG. 3 is a schematic diagram that depicts an exemplary hardware and software feedback loop that may be used to provide an accurate and constant flow of fluid to a site.

FIG. 3 schematically depicts an exemplary hardware and software feedback loop that may be used to provide an accurate and constant flow of oxygen to a patient in the embodiment of FIGS. 1A-1C. The feedback loop of FIG. 3 can also provide an accurate and constant flow of fluid to a site, such as the flow of inert gas to a clean room in the embodiment of FIG. 2. A RF signal may be a first signal from a remote control, e.g., to enter a desired flow rate, to increase the flow rate, or to decrease the flow rate. Typically, the signal is provided at a frequency in an unregulated industrial, scientific and medical (ISM) band. In addition, digital bit stream encoding such as frequency shift keying may be used to transmit the signal. In any case, the remote control signal should not interfere with other nearby wireless signals.

Meanwhile, the fluid flow sensor is positioned to detect and/or monitor fluid flowing therethrough. The flow sensor outputs an analog voltage that is directly proportional to the amount of flow through the device. The analog signal is then sent to an analog to digital converter (ADC) so that it can be processed by the microprocessor. The signal from the ADC is then used to determine whether the existing flow rate matches the desired flow-rate. If the software running on the microprocessor detects a difference between the existing and the desired flow rates, a signal is sent to the solenoid valve to adjust the flow rate accordingly. For example, a pulse width modulated (PWM) signal is a signal with a varying duty cycle, where the duty cycle is the amount of time that the signal is high versus the amount of time the signal is low. A PWM may be used to adjust the solenoid valve. The higher the duty cycle the more the valve will open and allow more fluid to flow through the system.

For portability, the remote control unit is preferably a handheld unit. In some instances, the remote control unit may be equipped to provide for fingertip adjustment of the rate of fluid flow. Fingertip control may be In addition or in the alternative, the remote control unit may be sound activated unit that is optionally equipped to provide for voice recognition adjustment of the rate of fluid flow. An analog and/or digital display may be included as well for indicating the rate of fluid flow.

As discussed above, the remote control unit should be effective to control the valve from a remote location. In general, the range should be equal to or greater than the length of the tube for fluid delivery. Regardless of the length of the tube, the remote control unit is typically effective for controlling the valve to a range of about 50 feet. Preferably, the remote control unit is effective for controlling the valve to a range of about 120 feet. Optimally the remote control unit is effective for controlling the valve to a range of about 300 feet. The actual range may depend on the location of use. For example, a typical American house is about 2,000 square feet in size. Thus, when the system of FIG. 1 is used in a typical American house, the remote control should be able to transmit at least 50 feet to remain functional throughout the house. In some instances, home use may require the remote control unit to have a transmission range up to 500 feet.

The remote control unit allows the user to change their fluid flow in order to receive the correct amount of fluid for their current needs. Preferably, the remote control unit is ergonomically designed so that it is easy to hold and use. For example, the remote control unit may be constructed to be worn like a wristwatch. In addition, lettering and display on the remote control should be large and easily visible so that people with impaired vision are able to read it at all times.

Figure 4A:
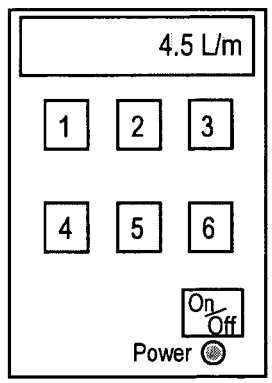
FIGS. 4A-4C collectively referred to as FIG. 4, depict exemplary remote control user interfaces.
Figure 4B:
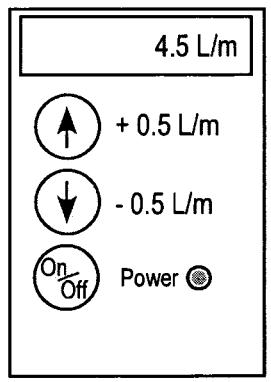
Figure 4C:
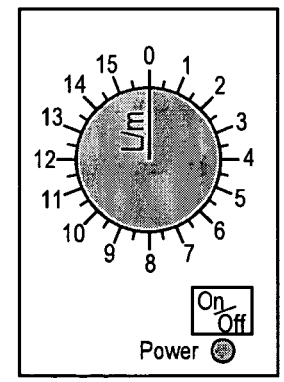

Exemplary user interfaces, e.g., provided by the remote control, are depicted in FIG. 4. For example, FIG. 4A depicts an interface that employs a button selection remote control. This interface utilizes a digital display to show the user the current fluid flow. The buttons below the display are used to input the desired flow. In addition, FIG. 4B depicts an interface that also uses a digital display to show the user the current fluid flow rate. Two buttons are provided on the remote to allow the user to change fluid flow rate. One of the buttons allows for the flow rate of fluid to be increased by preset increments while the other button is used to decrease the flow rate by the same preset value. Furthermore, FIG. 4C depicts a dial interface. When using this remote the user would use the dial to point to the desired fluid flow rate. This interface does not require a digital display because the flow-rates are displayed directly next to the dial.

Although the inventive system does not automatically adjust the rate of fluid flow, for the embodiment of FIGS. 1A-1C, a means for monitoring the level of blood oxygen or physical activity of the individual may be provided. In such instances, the system may also include an indicator for indicating the level of blood oxygen or physical activity monitored by the monitoring means. In general, a patient's oxygen saturation level should be at least 90%. Depending on the health and the activity level of an individual, the individual typically requires a flow rate between 0 and 15 liters per minute to keep his or her blood oxygen saturation level at 90% or higher.

A means for monitoring an individual's oxygen level is particularly advantageous for patients who suffer from COPD such as emphysema. For example, oxygen treatment is typically given to patients whose lung oxygen level is below 55 mm/Hg when resting or if the patient has an oxygen level below 60 mm/Hg and has other heart problems. Enough oxygen should be given to the patient to keep the level between 60 and 65 mm/Hg. Another consideration is that the oxygen during a plane ride in a depressurized cabin should be increased by 1-2 liters per minute. Such monitoring means may help in determining whether oxygen flow rate should be altered.

To monitor the oxygen saturation level in blood, pulse oximetry techniques may be employed. Pulse oximetry involves a measure of oxygen saturation in a patient's hemoglobin, and is a particularly useful diagnostics tool for monitoring patients who have problems absorbing oxygen into their blood from their lungs. Typically, oxygen saturation is measured via spectrophotometry. While oximetry may be carried out in either transmissive or reflective mode, both modes require a light source and a sensor, which are generally placed on an extremity, usually the finger, ear lobe, or the bridge of the nose, to sense the oxygen level in the blood. For example, a finger pulse oximeter may include two light emitting diodes (LEDs) at different wavelengths, 660 nanometers and 940 nanometers, and the sensor is a semiconductor detector, or a photodetector. These two wavelengths are associated with the absorbance wavelengths associated with deoxygenated and oxygenated hemoglobin, respectively.

As alluded to above, automatic adjustment mechanisms associated with oxygen delivery systems are often imperfect. Often, the response times associated with such mechanisms are inadequate and results in the delayed adjustment of oxygen delivery. For example, when oxygen first enters the body, it takes an additional 15-30 seconds for it to reach the extremities of the body. Thus, when an oximeter is used at the extremities for automatic adjustment of oxygen flow rate, the lag time for adjustment will be about 15-30 seconds. Accordingly, the invention provides a faster response time than an automatic adjusting system using oximetry. Nevertheless, pulse oximetry may provide the user with a quantitative measure of oxygen delivery.

When used in conjunction with oxygen and other flammable fluids, valves and other components of the invention must be constructed with safety precautions in mind. For instance, explosion-proof and/or watertight solenoid valves are commercially available. When one or more motors are used actuate a valve, any motors used should be non-sparking. That is, the motor must have no normally arcing parts or thermal effects capable of ignition. Examples of normally arcing parts include, but are not limited to, relays, circuit breakers, servopotentiometers adjustable resistors, switches, non-latching type connectors and motor brushes. Preferably, the motors are also explosion proof. That is, the motor may be enclosed in a case that is capable of withstanding an explosion of a specified fluid or vapor that may occur therein. Optimally, the motor is constructed to operate at sufficiently Iowan external temperature that a surrounding flammable atmosphere will not be ignited thereby. Explosion proof motors are available from manufacturers such as Teco-Westinghouse Motor Company (Round Rock, Tex.) and Rockwell Automation, Inc (Milwaukee, Wis.). Similarly, explosion-proof containers may be employed for containing the valve or any other component that may ignite a flammable medical fluid.

To promote safety and to maintain the proper functioning of the valve, the system may include a leak detector for detecting for a leak associated with the valve. Such a leak detector may represent a component of an error detection system. For example, the leak detector may be constructed to warn the user whenever a leak is detected; the user would then be warned to place the system into manual mode. Alternatively, the system could place itself into manual mode.

In addition, the error detection system may include failsafe modes of operation. For example, in case of system failure, the system may provide a warning signal and deliver oxygen at a pre-specified flow rate, e.g., determined by the patient's doctor. In addition, a means for emergency shutoff of the fluid flow may be provided as well.

In some instances, a monitoring station may be provided in addition to the remote control unit. Such a monitoring station may be stationary or mobile. For example, a monitoring system may be constructed as a workstation for controlling a plurality of valves and is equipped with an indicator for each valve controlled thereby. Such a workstation may be provided as standard equipment to allow a single user to monitor and adjust the fluid flow rates to a plurality of patients undergoing oxygen therapy. In addition, such a station may be interfaced to a computer. One of ordinary skill in the art will recognize that software may be developed for organizing, displaying, and or printing information about regarding oxygen usage.

Variations of the invention, not explicitly disclosed herein, will be apparent to those of ordinary skill in the art. For example, additional remote control units for controlling the valve may be provided. In such a case, a single control unit may override any signal from another control unit for controlling the valve. Furthermore, as provided in the embodiment of FIG. 2, the invention may be adapted to nonmedical applications, e.g., environmental controls.

It is to be understood that while the invention has been described in conjunction with the preferred specific embodiments thereof, that the foregoing description illustrates but does not limit the scope of the invention. Other aspects, advantages and modifications within the scope of the invention will be apparent to those skilled in the art to which the invention pertains.

All patents, patent applications, patent publications and non-patent literature references mentioned herein are incorporated by reference in their entireties.

The invention claimed is:

1. A fluid regulation system, comprising:
    a source configured to hold a fluid;
    a tube operatively connected to the source configured to deliver the fluid from the source to a site;
    a valve configured to control a rate of fluid delivered from the source to the site via the tube;
    a wireless remote control unit configured to enable a user to control the valve to adjust the rate of fluid delivered from the source to the site; and
    a display configured to indicate the rate of fluid delivered from the source to the site, wherein the rate of fluid delivered from the source to the site is measured by a flow sensor.

2. The fluid regulation system of claim 1 further comprising a receiver operatively interconnected with the valve configured to receive a control signal to control the valve.

3. The fluid regulation system of claim 2 wherein the control signal is sent from the remote control unit.

4. The fluid regulation system of claim 2 further comprising a flow sensor operatively interconnected to the valve configured to monitor an existing rate for the rate at which fluid is delivered from the source to the site.

5. The fluid regulation system of claim 4 wherein the flow sensor is further configured to detect that a desired rate for the rate of fluid delivered from the source to the site is different than the existing rate, the flow sensor further configured to send the control signal to the receiver to control the valve to adjust the existing rate to the desired rate in response to detecting the difference maintain the rate of fluid delivered from the source to the site using the control signal.

6. The fluid regulation system of claim 2 wherein the control signal comprises an electromagnetic signal.

7. The fluid regulation system of claim 6 wherein the electromagnetic signal comprises a radio frequency signal.

8. The fluid regulation system of claim 6 wherein the electromagnetic signal comprises a microwave signal.

9. The fluid regulation system of claim 6 where in the electromagnetic signal comprises an infrared signal.

10. The fluid regulation system of claim 6 wherein the electromagnetic signal comprises a visible signal.

11. The fluid regulation system of claim 2 wherein the remote control unit is operatively interconnected to the receiver.

12. The fluid regulation system of claim 2 wherein the remote control unit is operatively connected to the receiver through a wireless link.

13. The fluid regulation system of claim 1 wherein the fluid comprises oxygen.

14. The fluid regulation system of claim 1 wherein the remote control unit is sound activated.

15. The fluid regulation system of claim 1 further comprising a leak detector configured to detect a fluid leak of the system.

16. The fluid regulation system of claim 1 wherein the display is operatively interconnected to the remote control unit.

17. The fluid regulation system of claim 1 wherein the valve comprises a motor configured to adjust the rate of fluid delivered from the source to the site.

18. The fluid regulation system of claim 1 further comprising a first power source operatively connected to the valve configured to adjust the rate of fluid delivered from the source to the site.

19. The fluid regulation system of claim 18 further comprising a second power source operatively connected to the valve configured to adjust the rate of fluid delivered from the source to the site following a failure of the first power source.

20. The fluid regulation system of claim 18 wherein the valve enables manual control.

21. The fluid regulation system of claim 1 further comprising a monitoring station operatively connected to the valve configured to monitor the rate of fluid delivered from the source to the site and further configured to adjust the rate of fluid delivered from the source to the site.

22. The fluid regulation system of claim 1 wherein the remote control unit is further configured to adjust the rate to one or more preset rates.

23. The fluid regulation system of claim 1 wherein the system is configured to provide a warning signal in response to a failure of the system.

24. The fluid regulation system of claim 1 further comprising a flow sensor operatively interconnected to the valve configured to monitor the rate at which fluid is delivered from the source to the site.

25. The fluid regulation system of claim 1 wherein the valve comprises a solenoid valve.

26. The fluid regulation system of claim 1 further comprising an error detection system configured to detect an error in the system and further configured to control the valve to adjust the rate of fluid delivered to a pre-specified rate in response to detecting the error.

27. A method for operating a fluid regulation system, comprising:
holding a fluid by a source;
delivering the fluid from the source to a site via a tube operatively connected to the source;
controlling, with a valve operatively connected to the tube, a rate of fluid delivered from the source to the site via the tube;
enabling a user to control the valve to adjust the rate of fluid delivered from the source to the site using a wireless remote control unit; and
indicating at a display the rate of fluid delivered from the source to the site, wherein the rate of fluid delivered from the source to the site is measured by a flow sensor.

28. The method of claim 27 further comprising receiving a control signal by a receiver operatively interconnected with the valve to control the valve.

29. The method of claim 28 further comprising sending the control signal from the remote control unit.

30. The method of claim 28 further comprising monitoring an existing rate for the rate at which fluid is delivered from the source to the site with a flow sensor operatively interconnected to the valve.

31. The method of claim 30 further comprising:
detecting with the flow sensor that a desired rate for the rate of fluid delivered from the source to the site is different than the existing rate; and
sending the control signal to the receiver to control the valve to adjust the existing rate to the desired rate in response to detecting the difference.

32. The method of claim 27 wherein the control signal comprises an electromagnetic signal.

33. The method of claim 32 where in the electromagnetic signal comprises a radio frequency signal.

34. The method of claim 32 wherein the electromagnetic signal comprises a microwave signal.

35. The method of claim 32 wherein the electromagnetic signal comprises an infrared signal.

36. The method of claim 32 wherein the electromagnetic signal comprises a visible signal.

37. The method of claim 27 further comprising detecting a fluid leak of the system by a leak detector.

38. The method of claim 27 wherein the remote control unit is operatively interconnected to the receiver.

39. The method of claim 27 wherein the remote control unit is operatively connected to the receiver through a wireless link.

40. The method of claim 27 wherein the fluid comprises oxygen.

41. The method of claim 27 further comprising activating the remote control unit with sound.

42. The method of claim 27 wherein the display is operatively interconnected to the remote control unit.

43. The method of claim 27 further comprising controlling the valve using a motor to adjust the rate of fluid delivered from the source to the site.

44. The method of claim 27 further comprising adjusting the rate of fluid delivered from the source to the site using a first power source operatively connected to the valve.

45. The method of claim 44 further comprising adjusting the rate of fluid delivered from the source to the site using a second power source operatively connected to the valve following a failure of the first power source.

46. The method of claim 27 further comprising enabling manual control of the valve.

47. The method of claim 27 further comprising:
monitoring the rate of fluid delivered from the source to the site using a monitoring station operatively connected to the valve; and
adjusting the rate of fluid delivered from the source to the site using the monitoring station.

48. The method of claim 27 further comprising adjusting the rate to one or more preset rates using the remote control unit.

49. The method of claim 27 further comprising providing a warning signal at the system in response to a failure of the system.

50. The method of claim 27 further comprising monitoring the rate at which fluid is delivered from the source to the site using a flow sensor operatively interconnected to the valve.

51. The method of claim 27 wherein the valve comprises a solenoid valve.

52. The method of claim 27 further comprising:
detecting an error of the system; and
in response to detecting the error, controlling the valve to adjust the rate of fluid delivered to a pre-specified rate.

53. A fluid regulation system, comprising;
means for holding a fluid;
means for delivering the fluid from a source to a site;
means for controlling a rate of fluid delivered from the source to the site;
means for enabling a user to wirelessly control a valve to adjust the rate of fluid delivered from the source to the site; and
means for indicating the rate of fluid delivered from the source to the site, wherein the rate of fluid delivered from the source to the site is measured by a flow sensor.

54. The system of claim 53 further comprising means for receiving a control signal to control the valve.

55. The system of claim 54 further comprising means for sending the control signal to control the valve.

56. The system of claim 54 further comprising means for monitoring an existing rate for the rate at which fluid is delivered from the source to the site.

57. The system of claim 56 further comprising:
means for detecting that a desired rate for the rate of fluid delivered from the source to the site is different than the existing rate; and
means for adjusting the existing rate to the desired rate in response to detecting the difference.

58. The system of claim 53 wherein the control signal comprises an electromagnetic signal.

59. The system of claim 58 wherein the electromagnetic signal comprises a radio frequency signal.

60. The system of claim 58 wherein the electromagnetic signal comprises a microwave signal.

61. The system of claim 58 wherein the electromagnetic signal comprises an infrared signal.

62. The system of claim 58 where in the electromagnetic signal comprises a visible signal.

63. The system of claim 53 further comprising means for detecting a fluid leak of the system.

64. The system of claim 53 wherein the means for enabling is operatively interconnected to the receiver.

65. The system of claim 53 wherein the means for enabling is operatively connected to the receiver through a wireless link.

66. The system of claim 53 wherein the means for indicating is operatively interconnected to the means for enabling.

67. The system of claim 53 further comprising means for controlling the valve to adjust the rate of fluid delivered from the source to the site.

68. The system of claim 53 further comprising:
means for monitoring the rate of fluid delivered from the source to the site; and
means for adjusting the rate of fluid delivered from the source to the site.

69. The system of claim 53 further comprising means for adjusting the rate to one or more preset rates.

70. The system of claim 53 further comprising means for monitoring the rate at which fluid is delivered from the source to the site.

71. The system of claim 53 further comprising:
means for detecting an error of the system; and
means for controlling the valve to adjust the rate of fluid delivered to a pre-specified rate in response to detecting the error.

72. The fluid regulation system of claim 1 wherein the rate of fluid indicated on the display includes an integer.

73. The fluid regulation system of claim 1 wherein the rate of fluid indicated on the display includes lettering.

74. The method of claim 27 wherein the rate of fluid indicated on the display includes an integer.

75. The method of claim 27 wherein the rate of fluid indicated on the display includes lettering.

76. The system of claim 53 wherein the rate of fluid includes an integer.

77. The system of claim 53 wherein the rate of fluid includes lettering.

* * * * *